United States Patent [19]

Bird et al.

[11] Patent Number: 5,254,800
[45] Date of Patent: Oct. 19, 1993

[54] TOMATO PLANTS AND CELLS CONTAINING PTOM36 ANTISENSE CONSTRUCTS

[75] Inventors: Colin R. Bird, Berkshire; Donald Grierson, Loughbrough; John A. Ray, Bracknell; Wolfgang W. Schuch, Berkshire, all of England

[73] Assignee: Imperial Chemical Industries PLC, London, England

[21] Appl. No.: 598,873

[22] Filed: Oct. 19, 1990

[30] Foreign Application Priority Data

Oct. 20, 1989 [GB] United Kingdom ............... 8923716

[51] Int. Cl.$^5$ .................. A01H 4/00; C12N 5/14; C12N 15/82
[52] U.S. Cl. .................. 800/205; 435/320.1; 435/240.4; 800/250; 800/DIG. 44; 935/64; 935/67
[58] Field of Search .................. 435/320.1, 240.4; 800/205, 250, DIG. 44; 935/64, 67

[56] References Cited

U.S. PATENT DOCUMENTS 4,801,540  1/1989  Hiatt et al. .................. 435/172.3
5,107,065  4/1992  Shewmaker et al. .............. 800/205

OTHER PUBLICATIONS

Grierson et al. Gene expression during tomato ripending, Phil. Trans. R. Soc. Lond. B 314, 399–410 (1986).
Schuch et al. Control and manipulation of gene expression during tomato fruit ripening, Plant Molecular Biology, 13:303–311, 1989.
Slater, et al. (1985) Plant Molecular Biology 5: 137–147.
Maunders et al. (1987) Plant, Cell and Environment 10: 174–184.
Smith et al. (Aug. 1988) Nature 334: 724–726.

Primary Examiner—Che S. Chereskin
Attorney, Agent, or Firm—Cushman, Darby & Cushman

[57] ABSTRACT

DNA constructs comprise a DNA sequence homologous to some or all of the gene encoded by the clone pTOM36. The constructs may further comprise a transcriptional initiation region operative in plants for transcribing this DNA sequence, optionally in the antisense direction to produce mRNA complementary to the pTOM36 gene. Transformed plant cells and plants may be derived from such constructs: fruit from the plants (such as tomatoes) are expected to have modified ripening properties.

11 Claims, 3 Drawing Sheets

FIG. 1 NUCLEOTIDE SEQUENCE OF PTOM36

```
          10         20         30         40         50         60         70
) ATGGTAAATT GCAATGGTGA AGGAGTCTTG TTTATCGAAG GTGATGCTAA TATAGAGCTT GAAAAATTAG 80         90        100        110        120        130        140
  GTGAATCTAT TAAGCCACCA TGTCATACTT GGATTTACTA CTTCATAATG TTCATGGTTC TGATGGAATT 150        160        170        180        190        200        210
  ATTGGTTCTC CTCTTTTGTT AATTCAGGTG ACTCGTTTTA CTTGTGGTGG ATTTGCTGTT GGATTTAGAT 220        230        240        250        260        270        280
  TTAATCACAC AATGATGGAT GCTTATGGCT TCAAAATGTT TCTAAATGCG TTAAGTGAAT TAATTCAAGG 290        300        310        320        330        340        350
  AGCTTCAACA CCTTCTATAT TGCCTGTATG GGAAAGACAT CTCCTAAGTG CTAGATCATC ACCAAGTATT 360        370        380        390        400        410        420
  ACATGTATTC ATCATGAGTT TGATGAGGAA ATTGAATCAA AAATTGCGTG GGAATCTATG GAAGATAAGT 430        440        450        460        470        480        490
  TGATACAACA ATCATTTTTC TTTGGAAATG AGGAGATGGA AGTCATTAAA AATCAAGTTC CTCCAAATTA 500        510        520        530        540        550        560
  TGAATGTACA AAATTCGAGT TATTAATGGC ATTTTTATGG AAATGTCGTA CCATTGCTCT TAATTTGCAC 570        580        590        600        610        620        630
  TCTGATGAAA TTGTTCGTTT GACATACGTT ATTAATATAC GTGGAAAAAA GTCACTCAAC ATTGAATTAC 640        650        660        670        680        690        700
  CAATTGGTTA TTATGGGAAT GCGTTTATTA CTCCAGTTGT TGTATCAAAA GCAGGTTTGT TATGTTCAAA 710        720        730        740        750        760        770
  TCCAGTGACA TATGCAGTTG AATTGATCAA GAAAGTTAAA GATCATATAA ATGAAGAATA CATCAAATCA 780        790        800        810        820        830        840
  TTGATAGATT TAATGGTTAC TAAAGGGAGA CCAGAGTTAA CAAATCTTGG AATTTTTTGG TCTCAGATAA 850        860        870        880        890        900        910
  TAGATATATT GGATTTGATG AATTTGATTT TGGATGGGGA AACCCCATTT TTGGAGGGAT CTTAAAGGCT 920        930        940        950        960        970        980
  ATATCTTTCA CTAGTTTTGG TGTTTCTGTT AAAAATGACA AAGGAGAAAA AGGTGTTTTG ATAGCTATAA 990       1000       1010       1020       1030       1040       1050
  GTTTACCTCC ATTGGCCATG AAAAAACTTC AAGATATCTA CAACATGACT TTCAGAGTCA TAATTTCAAA 1060       1070       1080
  TATATAGGCT TTTCTATTGA AAAAAAAAA
```

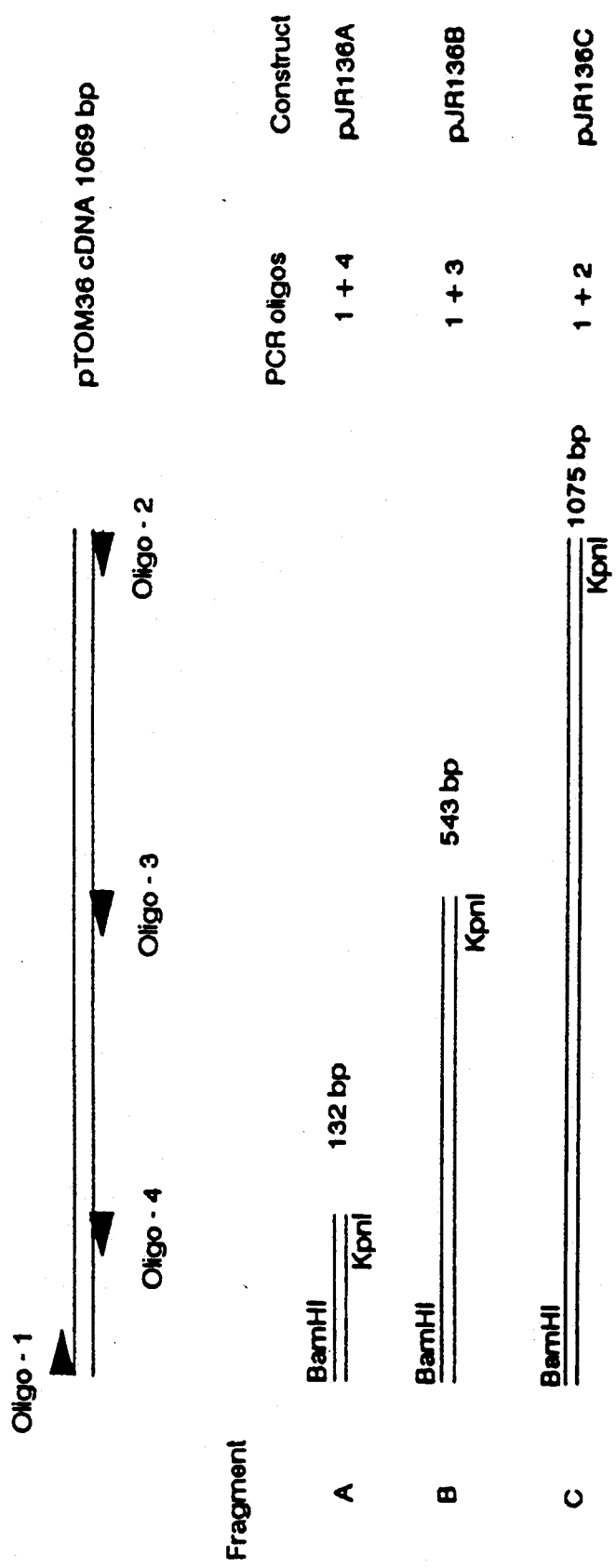
FIG. 2 Strategy used to synthesise BamHI-KpnI fragments by PCR from pTOM36

FIG. 3

Oligonucleotides used in PCR reactions with pTOM36 to synthesise BamHI-KpnI fragments for cloning into pJR1

| Oligo | 5' ........................................................ 3' |
|---|---|
| T36AS-1 | GGGGGGGATCCTAAATTGCAATGGTGAAGGAGTCTTG (** ) BamHI |
| T36AS-2 | GGTACCAATAGAAAAGCCTATATATTTGAAATTATGACTCTGAAAG (*****) KpnI |
| T36AS-3 | GGTACCGACATTTCCATAAAAATGCCATTAATAACTCGAATTTTGTACATTC (*****) KpnI |
| T36AS-4 | CCAATAATTCCATCGGTACCATGAACATTATGAAGTAGTAAATCCAAG (**) KpnI |

\* = base change or addition

TOMATO PLANTS AND CELLS CONTAINING PTOM36 ANTISENSE CONSTRUCTS

This application relates to novel DNA constructs, plant cells containing them and plants derived therefrom. In particular it involves the use of antisense RNA technology to control gene expression in plants.

As is well known, a cell manufactures protein by transcribing the DNA of the gene for that protein to produce messenger RNA (mRNA), which is then processed (e.g. by the removal of introns) and finally translated by ribosomes into protein. This process may be inhibited by the presence in the cell of "antisense RNA". By this term is meant an RNA sequence which is complementary to a sequence of bases in the mRNA in question: complementary in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, for example in European Patent publication no 271988 to ICI (corresponding to U.S. Ser. No. 119,614). Reduction of gene expression has led to a change in the phenotype of the plant: either at the level of gross visible phenotypic difference e.g. lack of anthocyanin production in flower petals of petunia leading to colourless instead of coloured petals (van der Krol et al, Nature, 333, 866-869, 1988); or at a more subtle biochemical level e.g. change in the amount of polygalacturonase and reduction in depolymerisation of pectins during tomato fruit ripening (Smith et al, Nature, 334, 724-726, 1988; Smith et al., manuscript submitted for publication). Thus antisense RNA has been proven to be useful in achieving downregulation of gene expression in plants.

In work leading to the present invention we have identified a gene which expresses an enzyme involved in the ripening of tomatoes. This gene has been cloned and characterised. We postulate that it will be of use in modifying the ripening tomatoes and other fruit. The gene in question is encoded (almost completely) in the clone pTOM36, not previously disclosed.

According to the present invention we provide DNA constructs comprising a DNA sequence homologous to some or all of the gene encoded by the clone pTOM36. The homologous DNA sequence may be preceded by a transcriptional initiation region operative in plants, so that the construct can generate mRNA in plant cells.

In a further aspect, the present invention provides DNA constructs comprising a transcriptional initiation region operative in plants positioned for transcription of a DNA sequence encoding RNA complementary to a substantial run of bases showing substantial homology to an mRNA encoding the enzyme produced by the gene in pTOM36. The invention also includes plant cells containing such constructs; plants derived therefrom showing modified ripening characteristics; and fruit and seeds of such plants.

The constructs of the invention may be inserted into plants to regulate the production of the pTOM36 enzyme. Depending on the nature of the construct, the production of the enzyme may be increased, or reduced, either throughout or at particular stages in the life of the plant. The plants to which the present invention can be applied include commercially important fruit-bearing plants, in particular the tomato. In this way, plants can be generated which may have one or more of the following characteristics:

Novel flavour and aroma due to changes in the concentrations and ratios of the many aromatic compounds that contribute to fruit flavour.

Sweeter fruit (e.g. tomatoes) due to decrease in the accumulation of acids (e.g. citric or malic acid) thereby allowing the flavour of the sugars to dominate.

Modified colour due to inhibition of the pathways of pigment biosynthesis (e.g. in the case of tomatoes, lycopene, $\beta$-carotene).

Longer shelf life and better storage characteristics due to reduced activity of degradative pathways (e.g. cell wall hydrolysis).

Improved processing characteristics due to changed activity of enzymes contributing to factors such as: viscosity, solids, pH, elasticity.

Modified fruit shape thus improving packing and storage characteristics.

Extended leaf biosynthetic activity due to inhibition of enzymes responsible for the degradative processes involved in senescence (in particular, leaf senescence); thus improving plant productivity.

DNA constructs according to the invention preferably comprise a homologous base sequence at least 50 bases in length. There is no theoretical upper limit to the base sequence—it may be as long as the relevant mRNA produced by the cell—but for convenience it will generally be found suitable to use sequence between 100 and 1000 bases in length. The preparation of such constructs is described in more detail below.

The preferred source of antisense RNA for use in the present invention is DNA derived from the clone pTOM36. The required DNA encoding antisense RNA can be obtained in several ways: by cutting with restriction enzymes an appropriate sequence of such DNA; by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences, the cloning being carried out so that the DNA sequence is inverted with respect to its orientation in the strand from which it was cut. In the new vector, the strand that was formerly the template strand becomes the coding strand, and vice versa. The new vector will thus encode RNA in a base sequence which is complementary to the sequence of pTOM36 mRNA. Thus the two RNA strands are complementary not only in their base sequence but also in their orientations (5' to 3').

As source of the DNA base sequence for transcription, it is convenient to use a cDNA clone such as pTOM36. The base sequence of pTOM36 is set out in FIG. 1. Searches in DNA and protein data bases have not revealed any homology to known genes or proteins. This clone has been deposited at the National Collections of Industrial and Marine Bacteria, PO Box 31, of 23 St Machar Drive (formerly of 135 Abbey Road), Aberdeen AB2 1RY, Scotland, as a plasmid in E.coli, under the reference NCIMB 40192, on Sep. 1, 1989. Alternatively, a cDNA clone similar to pTOM36 may be obtained from the mRNA of ripening tomatoes by the method described by Slater et al, Plant Molecular Biology 5, 137-147, 1985. In this way may be obtained sequences coding for the whole, or substantially the whole, of the mRNA produced by pTOM36. Suitable lengths of the cDNA so obtained may be cut out for use by means of restriction enzymes.

An alternative source of DNA for the base sequence for transcription is a suitable gene encoding a protein involved in fruit ripening. Such a gene may differ from the cDNA of pTOM36 in that introns may be present. The introns are not transcribed into mRNA (or, if so transcribed, are subsequently cut out). When using such a gene as the source of the base sequence for transcription it is possible to use either intron or exon regions.

A further way of obtaining a suitable DNA base sequence for transcription is to synthesise it ab initio from the appropriate bases, for example using FIG. 1 as a guide.

Recombinant DNA and vectors according to the present invention may be made as follows. A suitable vector containing the desired base sequence for transcription (for example pTOM36) is treated with restriction enzymes to cut the sequence out. The DNA strand so obtained is cloned (in reverse orientation) into a second vector containing the desired promoter sequence (for example cauliflower mosaic virus 35S RNA promoter or the tomato polygalacturonase gene promoter sequence—Bird et al., Plant Molecular Biology, 11, 651-662, 1988) and the desired terminator sequence (for example the 3' of the Agrobacterium tumefaciens nopaline synthase gene, the nos 3' end).

According to the invention we propose to use both constitutive promoters (such as cauliflower mosaic virus 35S RNA) and inducible or developmentally regulated promoters (such as the ripe-fruit-specific polygalacturonase promoter) as circumstances require. Use of a constitutive promoter will tend to effect functions in all parts of the plant: while by using a tissue specific promoter, functions may be controlled more selectively. Thus in applying the inventions, e.g. to tomatoes, it may be found convenient to use the promoter of the PG gene (Bird et al, 1988, cited above). Use of this promoter, at least in tomatoes, has the advantage that the production of antisense RNA is under the control of a ripening-specific promoter. Thus the antisense RNA is only produced in the organ in which its action is required. Other ripening-specific promoters that could be used include the E8 promoter (Diekman & Fischer, EMBO Journal 7, 3315-3320, 1988) and the promoters from the pTOM36 genes.

Vectors according to the invention may be used to transform plants as desired, to make plants according to the invention. Dicotyledonous plants, such as tomato, may be transformed by Agrobacterium Ti plasmid technology, for example as described by Bevan (1984) Nucleic Acid Research, 12, 8711-8721. Such transformed plants may be reproduced sexually, or by cell or tissue culture.

The degree of production of RNA in the plant cells can be controlled by suitable choice of promoter sequences, or by selecting the number of copies, or the site of integration, of the DNA sequences according to the invention that are introduced into the plant genome. In this way it may be possible to modify ripening or senescence to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Examples of genetically modified plants according to the present invention include, as well as tomatoes, fruits of such as mangoes, peaches, apples, pears, strawberries, bananas and melons.

As previously stated, the preferred source of antisense RNA for use in the present invention is DNA showing homology to the gene encoded by the clone pTOM36. pTOM36 was derived from a cDNA library isolated from ripe tomato RNA (Slater et al Plant Molecular Biology 5, 137-147, 1985). Four other clones (pTOM22, pTOM76, pTOM77, pTOM89) from the same library cross-hybridise to pTOM36 and probably contain related sequences. pTOM36 has been characterised by hybrid select translation, but there is some ambiguity about the results of these experiments. Slater et al (Plant Molecular Biology 5, 137-147, 1985) reported a product of 44kD, whereas (Maunders et al Plant, Cell and Environment 10, 177-184, 1987) found that it encodes a protein of approximately 52,000 daltons. DNA sequence analysis has demonstrated that the clone is 1069 bases long with an open reading frame of 271 codons. It is believed to encode a cytoplasmic protein, as no apparent leader sequence was detected using computer analysis of the amino acid sequence derived from the DNA sequence.

We have shown that the mRNA for which pTOM36 codes is expressed in ripening tomato fruit. No expression could be detected in green fruit. pTOM36 is expressed most strongly at the full orange stage of ripening. The level of mRNA then declines in line with the general decline in isosynthetic capacity of the ripening fruit. Expression of pTOM36 mRNA could also be induced by exposing mature green fruit to exogenous ethylene. The expression of pTOM36 is reduced in the ripening inhibitor (rin) tomato fruit ripening mutant which mature very slowly. pTOM36 related sequences are also expressed in senescing leaves.

The genomic locations of sequences homologous to pTOM36 have been identified using RFLP mapping: three loci in the tomato genome carry sequences homologous to pTOM36. It has also been shown by Southern blotting that the gene may be present as a small multigene family. The individual members of the multigene family may be expressed differentially in ripening fruit and during senescence. Although a considerable body of information on the structure and expression of the pTOM36 gene family is known, the biochemical function of this clone has not hitherto been elucidated. In the present invention, we use antisense RNA in order to determine the phenotype of transgenic tomato plants which show modified—increased or reduced—expression of pTOM36.

The invention will now be described further with reference to the accompanying drawings, in which:

FIG. 1 shows the base sequence of the clone pTOM36(SEQ ID NO: 1);

FIG. 2 shows the regions of the pTOM36 sequence which may be synthesised by polymerase chain reaction (PCR) and used in the construction of antisense RNA vectors according to the invention.

FIG. 3 shows the base sequence of the oligonucleotides used as primers (SEQ ID NO:2 to SEQ ID NO:5) for the polymerase chain reactions to synthesise the fragments illustrated in FIG. 2.

The following Examples illustrate aspects of the invention.

EXAMPLE 1

Identification of Base Sequence of pTOM36

The base sequence of pTOM36 has not previously been determined. The sequence was determined by standard DNA sequencing procedures and is shown in FIG. 1. Knowledge of this sequence is essential for determining the orientation of the open reading frame and for the subsequent construction of RNA antisense vectors.

EXAMPLE 2A

Construction of pTOM36 Antisense RNA Vectors with the CaMV 35S Promoter

A vector pJR136B was constructed using the sequence corresponding to Fragment B (bases 1-538) of the pTOM36 cDNA as shown in FIG. 2.

This fragment was synthesised in vitro using polymerase chain reactions with the synthetic oligonucleotides 1 and 3 as shown in FIG. 2 as primers and pTOM36 cDNA as template. The synthetic oligonucleotide primers were designed such that a BamHI restriction site was incorporated at the 5' end of the fragment and a KpnI site was incorporated at the 3' end of the fragment: base sequences are shown in FIG. 3. After cleavage of the fragment with BamHI and KpnI, it was cloned into the vector pJR1 which had previously been cut with KpnI and BamHI, to give a vector which was named pJR136B. pJR1 (Smith et al Nature 334, 724-726, 1988) is a Bin19 (Bevan, Nucleic Acids Research, 12, 8711-8721, 1984) based vector, which permits the expression of the antisense RNA under the control of the CaMV 35S promoter. This vector includes a nopaline synthase (nos) 3' end termination sequence.

After synthesis of the vector pJR136B, the structure and orientation of the pTOM36 sequence it contained were confirmed by DNA sequence analysis.

EXAMPLE 2B

Vectors pJR136A and pJR136C were prepared in the same way as pJR136B in Example 2A. They contain respectively bases 1 to 132 and bases 1 to 1069 (the complete cDNA) of pTOM36.

EXAMPLE 3A

Construction of pTOM36 Antisense RNA Vector with the Polygalacturonase Promoter.

The fragment produced in Example 2A by cleavage with BamHI and KpnI was also cloned into the vector pJR2 to give the clone pJR236B.

pJR2 is a Bin19 based vector, which permits the expression of the antisense RNA under the control of the tomato polygalacturonase promoter. This vector includes a nopaline synthase (nos) 3' end termination sequence. This vector does not contain a KpnI or a BamHI site between the promoter and terminator sequences. Consequently, the PCR synthesised fragment was digested with KpnI and BamHI, the cut ends were made flush with T4 polymerase and then cloned into the HincII site of pJR2. After synthesis, the vector with the correct inverted orientation of pTOM36 sequence was identified by DNA sequence analysis.

EXAMPLE 3B

Clones similar to pJR236B were made from the fragments of Example 2B. These are:
1. Bases 1 to 132—pJR236A
2. Bases 1 to 1069—pJR236C

EXAMPLE 4

Construction of pTOM36 sense RNA vectors with the CaMV 35 promoter.

The fragments of pTOM36 cDNA described in Example 2 were also cloned into the vector pJR1 in the sense orientation to give the following clones:
1. Bases 1 to 132—pJR136AS
2. Bases 1 to 538—pJR136BS
3. Bases 1 to 1069—pJR136CS The PCR generated fragments were digested with KpnI and BamHI, the cut ends made flush with T4 polymerase and then cloned into the HincII site of pJR1. After synthesis, the vectors with the sense orientation of pTOM36 sequence were identified by DNA sequence analysis.

EXAMPLE 5

Generation of Transformed Plants

Vectors were transferred to *Agrobacterium tumefaciens* LBA4404 (a micro-organism widely available to plant biotechnologists) and were used to transform tomato plants (*Lycopersicon esculentum*, var. Ailsa Craig). Transformation of tomato stem segments followed standard protocols (e.g. Bird et al Plant Molecular Biology 11, 651-662, 1988. Transformed plants were identified by their ability to grow on media containing the antibiotic kanamycin. Plants were regenerated and grown to maturity. Ripening fruit were analysed by PCR.

Where the vector used was pJR136B (prepared as in Example 2A) PCR reactions with genomic DNA from 11 transformants indicated that at least 10 of the plants contained the pTOM36 antisense construct from pJR136B. One such plant (coded $E_{56}C_6S_1$) was allowed to produce fruit. RNA analysis of orange fruit of this plant showed a lower level of 1.45 kb mRNA homologous to the endogenous pTOM36 gene as compared with similar fruit from an untransformed Ailsa Craig plant. However, the level of RNA homologous to pTOM6 (produced by the polygalacturonase gene) was similar in both fruit. We infer that this reduction in pTOM36 mRNA is caused by antisense RNA produced by DNA derived from the pJR136 construct.

We claim:

1. DNA constructs comprising a DNA sequence encoded by the clone pTOM36 which is preceded by a transcriptional initiation region operative in plants and positioned so that the construct can generate RNA complementary to pTOM36 mRNA in plant cells.

2. DNA constructs as claimed in claim 1 in which the DNA sequence is the sequence set forth in FIG. 1.

3. DNA constructs as claimed in claim 1 in which the transcriptional initiation region operative in plants is a constitutive promoter.

4. DNA constructs as claimed in claim 3 in which the constitutive promoter is CaMV 35S.

5. DNA constructs as claimed in claim 1 in which the transcriptional initiation region operative in plants is an inducible or developmentally regulated promoter.

6. DNA constructs as claimed in claim 5 in which the promoter is that for the polygalacturonase gene.

7. Tomato plant cells transformed with a construct claimed in claim 1.

8. Plants containing cells claimed in claim 7.

9. Plants claimed in claim 8 which bear climacteric fruit.

10. Fruit or seeds of plants claimed in claim 8.

11. Tomato seeds as claimed in claim 10 containing a construct adapted to express mRNA antisense to pTOM36.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 1080 base pairs
      ( B ) TYPE: nucleic acid
      ( C ) STRANDEDNESS: double
      ( D ) TOPOLOGY: linear ( i i ) MOLECULE TYPE: cDNA to mRNA ( i i i ) HYPOTHETICAL: NO ( v i ) ORIGINAL SOURCE:
      ( A ) ORGANISM: Lycopersicon esculentum
      ( B ) STRAIN: Ailsa Craig
      ( D ) DEVELOPMENTAL STAGE: Ripening ( x i ) SEQUENCE DESCRIPTION: SEQ ID NO:1:

| | | | | | | |
|---|---|---|---|---|---|---|
| ATGGTAAATT | GCAATGGTGA | AGGAGTCTTG | TTTATCGAAG | GTGATGCTAA | TATAGAGCTT | 60 |
| GAAAAATTAG | GTGAATCTAT | TAAGCCACCA | TGTCATACTT | GGATTTACTA | CTTCATAATG | 120 |
| TTCATGGTTC | TGATGGAATT | ATTGGTTCTC | CTCTTTTGTT | AATTCAGGTG | ACTCGTTTTA | 180 |
| CTTGTGGTGG | ATTTGCTGTT | GGATTTAGAT | TTAATCACAC | AATGATGGAT | GCTTATGGCT | 240 |
| TCAAAATGTT | TCTAAATGCG | TTAAGTGAAT | TAATTCAAGG | AGCTTCAACA | CCTTCTATAT | 300 |
| TGCCTGTATG | GGAAAGACAT | CTCCTAAGTG | CTAGATCATC | ACCAAGTATT | ACATGTATTC | 360 |
| ATCATGAGTT | TGATGAGGAA | ATTGAATCAA | AAATTGCGTG | GAATCTATG | GAAGATAAGT | 420 |
| TGATACAACA | ATCATTTTTC | TTTGGAAATG | AGGAGATGGA | AGTCATTAAA | AATCAAGTTC | 480 |
| CTCCAAATTA | TGAATGTACA | AAATTCGAGT | TATTAATGGC | ATTTTTATGG | AAATGTCGTA | 540 |
| CCATTGCTCT | TAATTTGCAC | TCTGATGAAA | TTGTTCGTTT | GACATACGTT | ATTAATATAC | 600 |
| GTGGAAAAAA | GTCACTCAAC | ATTGAATTAC | CAATTGGTTA | TTATGGGAAT | GCGTTTATTA | 660 |
| CTCCAGTTGT | TGTATCAAAA | GCAGGTTTGT | TATGTTCAAA | TCCAGTGACA | TATGCAGTTG | 720 |
| AATTGATCAA | GAAAGTTAAA | GATCATATAA | ATGAAGAATA | CATCAAATCA | TTGATAGATT | 780 |
| TAATGGTTAC | TAAAGGGAGA | CCAGAGTTAA | CAAATCTTGG | AATTTTTTGG | TCTCAGATAA | 840 |
| TAGATATATT | GGATTTGATG | AATTTGATTT | TGGATGGGGA | AACCCCATTT | TTGGAGGGAT | 900 |
| CTTAAAGGCT | ATATCTTTCA | CTAGTTTTGG | TGTTTCTGTT | AAAAATGACA | AAGGAGAAAA | 960 |
| AGGTGTTTTG | ATAGCTATAA | GTTTACCTCC | ATTGGCCATG | AAAAAACTTC | AAGATATCTA | 1020 |
| CAACATGACT | TTCAGAGTCA | TAATTTCAAA | TATATAGGCT | TTTCTATTGA | AAAAAAAAA | 1080 |

( 2 ) INFORMATION FOR SEQ ID NO:2:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

GGGGGGGATC CTAAATTGCA ATGGTGAAGG AGTCTTG     37

( 2 ) INFORMATION FOR SEQ ID NO:3:

( i ) SEQUENCE CHARACTERISTICS:
      ( A ) LENGTH: 46 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:3:

GGTACCAATA GAAAAGCCTA TATATTTGAA ATTATGACTC TGAAAG 46

( 2 ) INFORMATION FOR SEQ ID NO:4:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

GGTACCGACA TTTCCATAAA AATGCCATTA ATAACTCGAA TTTTGTACAT TC 52

( 2 ) INFORMATION FOR SEQ ID NO:5:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

CCAATAATTC CATCGGTACC ATGAACATTA TGAAGTAGTA AATCCAAG 48